United States Patent [19]

Lagrange et al.

[11] Patent Number: 5,217,709
[45] Date of Patent: Jun. 8, 1993

[54] SUNSCREENING COMPOSITIONS CONTAINING 5-BENZYLIDENE-3-OXACYCLOPENTANONE

[75] Inventors: Alain Lagrange, Chatou; Serge Forestier, Claye-Souilly; Gerard Lang, Saint-Gratien; Bernadette Luppi, Sevran, all of France

[73] Assignee: L'Oreal, Paris, France

[21] Appl. No.: 426,427

[22] Filed: Oct. 24, 1989

[30] Foreign Application Priority Data

Oct. 28, 1988 [FR] France ............................ 88 14203

[51] Int. Cl.$^5$ .......................... A61K 7/42; A61K 9/10; A61K 9/12
[52] U.S. Cl. ............................................. 424/47; 8/405; 8/406; 424/DIG. 5; 424/59; 424/60; 424/61; 424/62; 424/63; 424/64; 424/70; 424/71; 424/72; 424/73; 514/844; 514/845; 514/847; 514/873; 514/937; 514/938; 514/944; 549/331; 549/472; 549/475
[58] Field of Search ................................ 424/59, 60

[56] References Cited

U.S. PATENT DOCUMENTS

| 2,104,492 | 1/1938 | Merkel et al. | 424/59 |
| 2,276,204 | 3/1942 | Kilgore | 424/59 |
| 2,334,348 | 11/1943 | Miglarise | 424/59 |
| 2,965,578 | 12/1960 | Pestemer et al. | 424/59 |

FOREIGN PATENT DOCUMENTS

| 0055976 | 1/1981 | European Pat. Off. | 424/59 |
| 0044970 | 7/1981 | European Pat. Off. | 424/59 |
| 0057882 | 1/1982 | European Pat. Off. | 424/59 |
| 2395023 | 6/1968 | France | 424/59 |

OTHER PUBLICATIONS

*Chemical Abstracts*, vol. 88, 1978, p. 608, Resume No. 152593a, Columbus, Ohio, U.S.A. & JP-A-77 153 994 (Sankyo Co., Ltd.) Dec. 21, 1977.

*Primary Examiner*—Dale R. Ore
*Attorney, Agent, or Firm*—Marshall, O'Toole, Gerstein, Murray & Bicknell

[57] ABSTRACT

Cosmetic composition containing, by way of a compound screening cut UV of wavelengths 280–380 nm, a 5-benzylidene-3-oxacyclopentanone of formula (I):

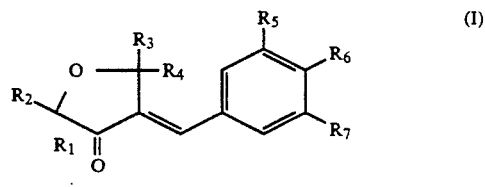

where
$R_1$, $R_2$, $R_3$ and $R_4$ denote $C_1$–$C_8$ alkyl, aralkyl or aryl, or alternatively $R_1$ and $R_2$ and/or $R_3$ and $R_4$ form, with the carbon to which they are attached, a saturated 5- or 6-membered ring, and
$R_5$, $R_6$ and $R_7$ denote H, $C_1$–$C_8$ alkyl, $C_2$–$C_8$ alkenyl, $C_1$–$C_{12}$ alkoxy, $C_2$–$C_8$ alkenyloxy, $C_2$–$C_{12}$ acyloxy, benzyloxy or —$COOR_{10}$ where $R_{10}$ is a $C_1$–$C_8$ alkyl, hydrogen, an alkali metal or alkaline earth metal or a radical derived from an amine, it also being possible for one of the substituents $R_5$, $R_6$ and $R_7$ to denote a radical

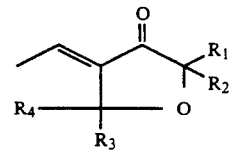

where $R_1$, $R_2$, $R_3$ and $R_4$ have the above meanings. This composition can be a protective composition for the human epidermis or the hair or an antisun composition.

New compounds of formula (I) in which $R_1$, $R_2$, $R_3$, $R_4$, $R_5$, $R_6$ and $R_7$, have the same meanings, $R_6$ being other than hydrogen, methyl and methoxy.

7 Claims, No Drawings

SUNSCREENING COMPOSITIONS CONTAINING 5-BENZYLIDENE-3-OXACYCLOPENTANONE

The present invention relates to screening cosmetic compositions, to their use for the protection of the skin and hair against ultraviolet radiation, to new 5-benzylidene-3-oxacyclopentanone derivatives used in these compositions and to a process for preparing them.

It is known that light radiation of wavelengths between 280 nm and 400 nm permit tanning of the human epidermis, and that rays of wavelengths between 280 and 320 nm, known by the designation UV-B, cause erythema and burning of the skin which can impair the development of the tan; this UV-B radiation must hence be screened out.

It is also known that UV-A rays, of wavelengths between 320 and 400 nm, causing tanning of the skin, are liable to induce an adverse change in the latter, in particular in the case of sensitive skin or skin continually exposed to solar radiation. UV-A rays cause, in particular, a loss of elasticity of the skin and the appearance of wrinkles, leading to premature ageing. They promote triggering of the erythematous reaction or enhance this reaction in some subjects, and can even be the source of phototoxic or photoallergic reactions.

It is hence advantageous to have the use of compounds capable of absorbing both UV-A rays and UV-B rays harmful to the skin.

It is also desirable to provide the hair with good protection against photochemical degradation in order to avoid a change in hue, bleaching or degradation of its mechanical properties.

It is known, moreover, that the constituents participating in cosmetic preparations do not always possess sufficient light-fastness and degrade through the action of light radiation.

Accordingly, it is desirable to incorporate in these preparations compounds capable of screening out UV rays, and which must show, in addition, good stability and sufficient solubility in the media customarily used in cosmetics.

During his investigations, the Applicant discovered, surprisingly, that certain 5-benzylidene-3-oxacyclopentanone derivatives showed, apart from good screening properties in the wavelength range extending from 280 to 380 nm, good chemical and photochemical stability. These compounds also have the advantage of not being toxic or irritant and of being completely harmless with respect to the skin. The compounds according to the invention, water-soluble or fat-soluble, also show good solubility in the usual cosmetic solvents The subject of the present invention is hence a cosmetic composition comprising, in a cosmetically acceptable vehicle, by way of an agent screening out ultraviolet radiation of wavelengths between 280 and 380 nm, an effective amount of at least one 5-benzylidene-3-oxacyclopentanone derivative having the following general formula:

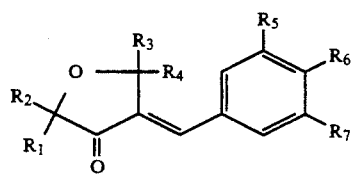

(I)

in which:

$R_1$, $R_2$, $R_3$ and $R_4$, which may be identical or different, denote a linear or branched $C_1$–$C_8$ alkyl residue, an aralkyl residue such as benzyl, unsubstituted or substituted with halogen atoms or with $C_1$–$C_4$ alkyl or alkoxy groups, or an aryl residue such as phenyl, unsubstituted or substituted with halogen atoms or with $C_1$–$C_4$ alkyl or alkoxy residues, or alternatively $R_1$ and $R_2$ and/or $R_3$ and $R_4$ form, with the carbon atom to which they are attached, a saturated ring containing 5 or 6 carbon atoms; and $R_5$, $R_6$ and $R_7$, which may be identical or different, denote a hydrogen atom, a linear or branched $C_1$–$C_8$ alkyl residue, a linear or branched $C_2$–$C_8$ alkenyl residue, a linear or branched $C_1$–$C_{12}$ alkoxy residue, a linear or branched $C_2$–$C_8$ alkenyloxy residue, a linear or branched $C_2$–$C_{12}$ acyloxy residue, a benzyloxy residue unsubstituted or substituted with halogen atoms or with $C_1$–$C_4$ alkyl or alkoxy residues, or alternatively a residue –$COOR_{10}$ where $R_{10}$ denotes a hydrogen atom, a linear or branched $C_1$–$C_8$, alkyl residue, an alkali metal or alkaline earth metal or a residue derived from an amine; one of the substituents $R_5$, $R_6$ and $R_7$ can also denote a radical of formula:

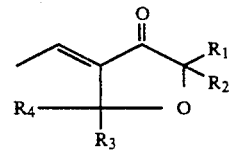

in which $R_1$, $R_2$, $R_3$ and $R_4$ have the meanings stated above.

It is, of course, understood that the compounds of formula (I) above can give rise to "cis-trans" isomerism around one or more double bond(s), and that all the isomers form part of the invention.

Among preferred compounds of general formula (I) used in the screening cosmetic composition according to the invention, there may be mentioned:

5-benzylidene-3-oxa-2,2,4,4-tetramethylcyclopentanone, 5-(4'-hexyloxybenzylidene)-3-oxa-2,2,4,4-tetramethylcyclopentanone, 5-(4'-allyloxybenzylidene)-3-oxa-2,2,4,4-tetramethylcyclopentanone, 5-(4'-octyloxybenzylidene)-3-oxa-2,2,4,4-tetramethylcyclopentanone, 5-(3',4',5'-tribenzyloxybenzylidene)-3-oxa-2,2,4,4tetramethylcyclopentanone, 5-(4'-tert-butoxybenzylidene)-3-oxa-2,2,4,4-tetramethylcyclopentanone, 5-(4'-methoxycarbonylbenzylidene)-3-oxa-2,2,4,4tetramethylcyclopentanone, 5-(4'-n-butoxy-5'-methoxybenzylidene)-3-oxa-2,2,4,4tetramethylcyclopentanone, 1,4-bis [(2',4',4'-tetramethyl-5'-oxo-3,-oxa-1'-cyclopentylidene)methyl]benzene, 4-[(2',2', 4',4'-tetramethyl-5'-oxo-3'-oxa-1'-cyclo-pentylidene)methyl]benzoic acid.

The compounds (I) are soluble in oils, except in the case where one of the radicals $R_5$, $R_6$ or $R_7$ denotes —$COOR_{10}$ in which $R_{10}$ denotes a hydrogen atom or an alkali metal or alkaline earth metal.

Depending on the nature of the substituents $R_5$, $R_6$ and $R_7$, the compounds of formula (I) have absorption maxima in the UV-B range (280-320 nm) or in the UV-A range (320-380 nm).

The subject of the present invention is also a process for protecting the skin and natural or sensitized hair against solar radiation, consisting in applying on the skin or the hair an effective amount of a cosmetic composition containing at least one 5-benzylidene-3oxacyclopentanone derivative of formula (I) above.

"Sensitized hair" is understood to mean hair which has undergone a permanent waving, dyeing or bleaching treatment.

The invention also relates to a light-stabilized, coloured or uncoloured cosmetic composition comprising an effective amount of at least one 5-benzylidene-3-oxacyclopentanone derivative of formula (I) above.

The subject of the invention is also the new 5-benzylidene-3-oxacyclopentanone derivatives of the following general formula (I'):

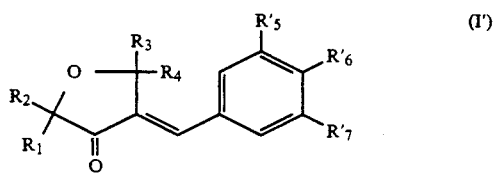

in which:

$R_1$, $R_2$, $R_3$ and $R_4$ have the same meanings as in the formula (I); $R'_5$ and $R'_7$, which may be identical or different, denote a hydrogen atom, a linear or branched $C_1$-$C_8$ alkyl residue, a linear or branched $C_2$-$C_8$ alkenyl residue, a linear or branched $C_1$-$C_{12}$ alkoxy residue, a linear or branched $C_2$-$C_8$ alkenyloxy residue, a linear or branched $C_2$-$C_{12}$ acyloxy residue, a benzyloxy residue unsubstituted or substituted with halogen atoms or $C_1$-$C_4$ alkyl or alkoxy groups, or a residue —$COOR_{10}$ where $R_{10}$ denotes a hydrogen atom, a linear or branched $C_1$-$C_8$ alkyl radical, an alkali metal or alkaline earth metal or a radical derived from an amine; and $R'_6$ denotes a linear or branched $C_2$-$C_8$ alkyl residue, a linear or branched $C_2$-$C_8$ alkenyl residue, a linear or branched $C_2C_{12}$ alkoxy residue, a linear or branched $C_2$-$C_8$ alkenyloxy residue, a linear or branched $C_2$-$C_{12}$ acyloxy residue, a benzyloxy residue unsubstituted or substituted with halogen atoms or $C_1$-$C_4$ alkyl or alkoxy groups, a residue —$COOR_{10}$ where $R_{10}$ denotes a linear or branched $C_1$-$C_8$ alkyl radical, a hydrogen, alkali metal or alkaline earth atom or a radical derived from an amine, or alternatively a radical of formula:

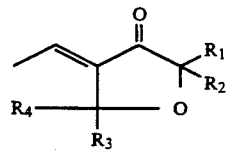

where $R_1$, $R_2$, $R_3$ and $R_4$ have the meanings stated above for the formula (I).

The compounds of formula (I,) possessing at least one of the following features are more especially preferred: $R_1$, $R_2$, $R_3$ and $R_4$ are methyl radicals, $R'_5$ and $R'_7$ denote a hydrogen atom or a benzyloxy or methoxy radical, and $R'_6$ denotes a n-butoxy, tert-butoxy, hexyloxy, octyloxy, allyloxy, benzyloxy, methoxycarbonyl, (2,2,4-tetramethyl-5-oxo-3-oxa-1-cyclopentylidene)methyl or carboxy radical.

Among the new compounds of formula (I'), the following preferred compounds may be mentioned:

5-(4'-hexyloxybenzylidene)-3-oxa-2,2,4,4-tetramethylcyclopentanone, 5-(4'- allyloxybenzylidene)-3-oxa-2,2,4,4-tetramethylcyclopentanone, 5-(4'-octyloxybenzylidene)-3-oxa-2,2,4,4-tetramethylcyclopentanone, 5-(3',4',5'-tribenzyloxybenzylidene)-3-oxa-2,2,4,4-tetramethylcyclopentanone, 5- (4'-tert-butoxybenzylidene)-3-oxa-2,2,4,4-tetramethylcyclopentanone, 5- (4'-methoxycarbonylbenzylidene)-3-oxa-2,2,4,4-tetramethylcyclopentanone, 5- (4'-methoxycarbonylbenzylidene)-3-oxa-2,2,4,4-tetramethylcyclopentanone, 5- (4'-n-butoxy-5'-methoxybenzylidene)-3-oxa-2,2,4,4-tetramethylcyclopentanone, 1,4-bis[(2',2', 4', 4'-tetramethyl-5'-oxo-3'-oxa-1'-cyclopentylidene)methyl]benzene, 4-[(2',2',4',4'-tetramethyl-5'-oxo-3'-oxa-1'-cyclopentylidene)methyl]benzoic acid.

The compounds of formula (I) or (I') are obtained by the condensation of an aromatic aldehyde of formula (II) or (II') with a 3-oxacyclopentanone of formula (III):

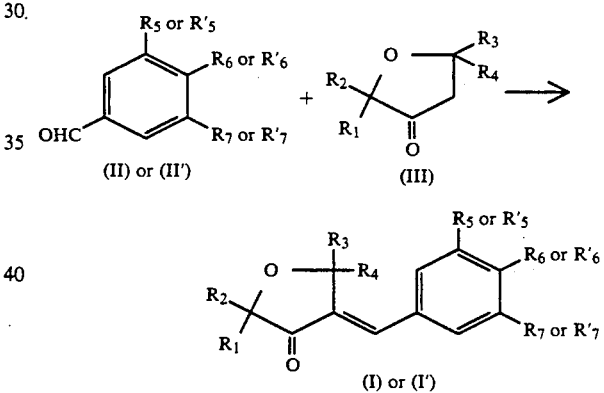

In the compounds of formula (II), (II') and (III), the substituents $R_1$ to $R_7$ or $R_1$ to $R'_7$ have the meanings stated above for the compounds of formula (I) and (I').

The aldehydes of formula (II) or (II') are known compounds. The 3-oxacyclopentanones of formula (III) may be prepared according to the methods described by C. SANDRIS and G. OURISSON, Bull. Soc. Chim. Fr. (1956), p.958 and by I. K. KOROBITSYNA et al., Zhur. Obschei Khim. Vol. 25, p. 734–738 and Vol. 27, p 1792–1795.

The condensation of the aldehyde (II) or (II') with the 3-oxacyclopentanone (III) may be carried out according to one of the following two processes:

FIRST PROCESS

The condensation is performed in the presence of an alkali metal alcoholate such as sodium methylate or potassium tert-butylate in a solvent such as toluene or 1,2-dimethoxyethane, at a temperature between −78° C. and the boiling point of the solvent. The condensation may also be performed in the presence of an inorganic base such as an alkali metal amide or hydride in a solvent such as 1,2-dimethoxyethane, or an alkali metal hydroxide in an alcohol, at a temperature between 0° C. and the boiling point of the reaction mixture.

SECOND PROCESS

The condensation of the aldehyde (II) or (II') with the 3-oxacyclopentanone (III) is performed in the presence of a borane of the following formula (IV):

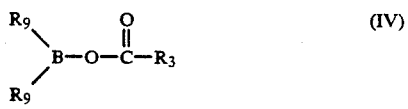

in which $R_8$ denotes a $C_1$-$C_6$ alkyl residue and $R_9$ denotes a $C_1$-$C_4$ alkyl residue. This compound is obtained according to the procedure described by L.H. TO-PORCER et al., J. Am. Chem. Soc. Vol. 87, p. 1236, (1965). Its isolation and purification are unnecessary for carrying out the condensation of the aldehyde (II) or (II') with the 3- oxacyclopentanone (III).

The condensation reaction is performed at a temperature of approximately 150° C., without a solvent.

The compounds (I) or (I') in which one of the radicals $R_5$, $R_6$ or $R_7$ or $R'_5$ to $R'_7$, denotes a residue —$COOR_{10}$ in which $R_{10}$ denotes a hydrogen atom are obtained by saponification of the corresponding esters.

The subject of the present invention is hence also the process for preparing the new compounds of formula (I').

The cosmetic composition of the invention may be used as a protective composition for the human epidermis or the hair, or as an antisun composition.

When used as a composition designed to protect the human epidermis against ultraviolet rays, the cosmetic composition according to the invention may be presented in the most diverse forms customarily used for this type of composition. It may, in particular, be presented in the form of a lotion, emulsion such as a cream or milk, oil, gel or solid stick, or be packaged as an aerosol.

It can contain the cosmetic adjuvants customarily used in this type of composition, such as thickeners, emollients, humectants, surfactants, preservatives, antifoams, fragrances, oils, waxes, lanolin, propellants, colourings and/or pigments whose function is to colour the composition itself or the skin or any other ingredient customarily used in cosmetics.

The compound of formula (I) is present in proportions of between 0.25 and 3% by weight relative to the total weight of the protective cosmetic composition for the human epidermis.

As a solubilization solvent, it is possible to use an oil, a wax and, generally speaking, any fat, a lower monohydric alcohol or polyol or a mixture thereof. More especially preferred monohydric alcohols or polyols are ethanol, isopropanol, propylene glycol, glycerol and sorbitol.

An embodiment of the invention is an emulsion in the form of a protective cream or milk comprising, in addition to the compound of formula (I), fatty alcohols, fatty acid esters and, in particular, fatty acid triglycerides, fatty acids, lanolin, natural or synthetic oils or waxes and emulsifiers, in the presence of water.

Another embodiment consists of oily lotions based on natural or synthetic oils and waxes, lanolin and fatty acid esters, in particular fatty acid triglycerides, or of oleo-alcoholic lotions based on a lower alcohol such as ethanol or a glycol such as propylene glycol and/or a polyol such as glycerol, and oils, waxes and fatty acid esters such as fatty acid triglycerides.

The cosmetic composition of the invention can also be an alcoholic or aqueous-alcoholic gel comprising one or more lower alcohols or polyols such as ethanol, propylene glycol or glycerol and a thickener such as silica, optionally in the presence of water. The oleoalcoholic gels contain, in addition, a natural or synthetic oil or wax.

The solid sticks consist of natural or synthetic waxes and oils, fatty alcohols, fatty acid esters, lanolin and other fats.

The present invention also relates to the antisun cosmetic compositions containing at least one compound of formula (I), which may be combined with other UV-B and/or UV-A screening agents.

In this case, the total quantity of screening agents present in the antisun composition is between 0.5 and 15% by weight relative to the total weight of the composition. These antisun cosmetic compositions are presented in the same forms as the compositions designed to protect the human epidermis described above.

When the cosmetic composition according to the invention is designed to protect natural or sensitized hair against UV rays, this composition may be presented in the form of a shampoo, lotion, gel or emulsion to be rinsed, to be applied before or after shampooing, before or after dyeing or bleaching and before or after permanent-waving, a styling or treatment lotion or gel, a blow-drying or setting lotion or gel, a hair lacquer or a permanent-waving or hair dyeing or bleaching composition. It contains 0.25 to 4% by weight of compound of formula (I).

The present invention also relates to coloured or uncoloured cosmetic compositions containing at least one compound of formula (I) by way of an agent for protection against UV rays.

These compositions can consist of hair products such as hair lacquers, setting lotions, optionally with a treating or disentangling action, shampoos, colouring shampoos or hair dyeing compositions, or of make-up products such as nail varnishes, treatment creams for the epidermis, foundations or lipsticks, as well as of any cosmetic composition capable of showing problems of light-fastness during storage as a result of its constituents. They contain 0.25 to 3% by weight of compound of formula (I).

The invention is illustrated by the non-limiting examples below.

PREPARATION EXAMPLES

EXAMPLE 1

5-(4'-Hexyloxybenzylidene)-3-oxa-2,2,4,4-tetramethylcyclopentanone

Preparation of a compound of general formula (I') in which $R_1=R_2=R_3=R_4=CH_3$, $R'_5=R'_7=H$ and $R'_6=-O-C_6H_{13}$ 104 g of 2,2,4,4-tetramethyl-3-oxacyclopentanone (0.72 mole) are dissolved in 100 cm$^3$ of 1,2-dimethoxyethane. The mixture is cooled to about 5° C. and 39 g (0.72 mole) of sodium methylate are then added with stirring. A solution of 134 g (0.65 mole) of 4-hexyloxybenzaldehyde in 100 cm$^3$ of 1,2-dimethoxyethane is introduced dropwise at a temperature of between 5° and 10° C. The reaction mixture is stirred for 3 hours at a temperature in the region of 0° C. and then poured into ice-cold water. The precipitate is filtered off, washed copiously with water and dried under reduced pressure. After recrystallization in heptane, the expected product takes the form of pale yellow crystals possessing the following characteristics:

| Melting point: | 63° C. |
| UV spectrum (chloroform): | $\lambda_{max}$: 335 nm |
| | $\epsilon$: 23000 |
| Elemental analysis: | $C_{21}H_{30}O_3$ |

| | C % | H % | O % |
| --- | --- | --- | --- |
| Calculated | 76.33 | 9.15 | 14.52 |
| Found | 76.19 | 9.17 | 14.80 |

EXAMPLE 2

5-Benzylidene-3-oxa-2,2,4,4-tetramethylcyclopentanone

Preparation of a compound of general formula (I) in which $R_1=R_2=R_3=R_4=CH_3$ and $R_5=R_6=R_7=H$ This compound is obtained according to the procedure described in Example 1, in which 4-hexyloxybenzaldehyde is replaced by benzaldehyde. The product obtained prosesses of the following characteristics:

| Melting point: | 78° C. |
| UV spectrum (dichloromethane): | $\lambda_{max}$: 299 nm |
| | $\epsilon$: 14600 |
| Elemental analysis: $C_{15}H_{18}O_2$ | |

| | C % | H % | O % |
| --- | --- | --- | --- |
| Calculated | 78.23 | 7.88 | 13.89 |
| Found | 77.66 | 7.96 | 14.46 |

EXAMPLE 3

5-(4'-Allyloxybenzylidene)-3-oxa-2,2,4,4-tetramethylcyclopentanone

Preparation of a compound of general formula (I') in which $R_1=R_2=R_3=R_4=CH_3, R'_5=R'_7=H$ and $R'_6=-O-CH_2-CH=CH_2$ This compound is obtained according to the procedure described in Example 1, in which 4-hexyloxybenzaldehyde is replaced by 4-allyloxybenzaldehyde. The compound obtained possesses the following characteristics:

| Melting point: | 82° C. |
| UV spectrum (dichloromethane): | $\lambda_{max}$: 330 nm |
| | $\epsilon$: 23450 |
| Elemental analysis: | $C_{18}H_{22}O_3$ |

| | C % | H % | O % |
| --- | --- | --- | --- |
| Calculated | 75.50 | 7.74 | 16.76 |
| Found | 75.03 | 7.75 | 17.41 |

EXAMPLE 4

5-(4'-Octyloxybenzylidene)-3-oxa-2,2,4,4-tetramethylcyclopentanone

Preparation of a compound of general formula (I') in which $R_1=R_2=R_3=R_4=CH_3$,  $=CH_3, R'_5=R'_7=H$ and $R'_6=-O-C_8H_{17}$ This compound is obtained according to the procedure described in Example 1, in which 4-hexyloxybenzaldehyde is replaced by 4-octyloxybenzaldehyde. The product obtained possesses the following characteristics:

| Melting point: | 50° C. |
| UV spectrum (dichloromethane): | $\lambda_{max}$: 332 nm |
| | $\epsilon$: 23350 |
| Elemental analysis: | $C_{23}H_{34}O_3$ |

| | C % | H % | O % |
| --- | --- | --- | --- |
| Calculated | 77.09 | 9.50 | 13.41 |
| Found | 77.11 | 9.62 | 13.41 |

| Melting point: | 73-75° C. |
| UV spectrum (dichloromethane): | $\lambda_{max}$: 340 nm |
| | $\epsilon$: 11410 |
| Elemental analysis: | $C_{36}H_{36}O_5$ |

| | C % | H % | O % |
| --- | --- | --- | --- |
| Calculated | 78.81 | 6.61 | 14.58 |
| Found | 78.78 | 6.61 | 14.64 |

EXAMPLE 6

5-(4'-tert-Butoxybenzylidene)-3-oxa-2,2,4,4-tetramethylcyclopentanone

Preparation of a compound of general formula (I') in which $R_1=R_2=R_3=R_4=CH_3, R'_5=R'_7=H$ and $R'_6$, $=-O-tert-butyl$ This compound is obtained according to the procedure described in Example 1, in which 4-hexyloxybenzaldehyde is replaced by 4-tert-butoxybenzaldehyde. The product obtained possesses the following characteristics:

| Melting point: | 72° C. |
| UV spectrum (dichloromethane): | $\lambda_{max}$: 326 nm |
| | $\epsilon$: 34275 |
| Elemental analysis: | $C_{19}H_{26}O_3$ |

| | C % | H % | O % |
| --- | --- | --- | --- |
| Calculated | 75.46 | 8.67 | 15.87 |
| Found | 74.83 | 8.72 | 16.49 |

EXAMPLE 7

5-(4'-Methoxycarbonylbenzylidene)-3-oxa-2,2,4,4-tetramethylclopentanone

Preparation of a compound of general formula (I') in which $R_1,=R_2=R_3=R_4=CH_3, R'_5=R'_7=H$ and $R'_6=-CO_2CH_3$ This compound is obtained according to the procedure described in Example 1, in which 4-hexyloxybenzaldehyde is replaced by methyl 4-formylbenzoate. The product obtained possesses the following characteristics:

| Melting point: | 108-110° C. |
| UV spectrum (dichloromethane): | $\lambda_{max}$: 300 nm |
| | $\epsilon$: 16200 |
| Elemental analysis: | $C_{17}H_{20}O_4$ |

| | C % | H % | O % |
| --- | --- | --- | --- |
| Calculated | 70.81 | 6.99 | 22.19 |
| Found | 70.67 | 7.06 | 22.28 |

EXAMPLE 8

5-(4'-n-Butoxy-5'methoxybenzylidene)-3-oxa-2,2,4,4-tetramethylcyclopentanone

Preparation of a compound of general formula (I') in which
$R_1=R_2=R_3=R_4=CH_3, R'_5=H, R'_6=\text{—O—}C_4H_9$ and $R'_7=\text{—OCH}_3$ This compound is obtained according to the procedure described in Example 1, in which 4-hexyloxybenzaldehyde is replaced by 4-butoxy-3-methoxybenzaldehyde. The product obtained possesses the following characteristics:

| Melting point: | 102° C. |
| --- | --- |
| UV spectrum (chloroform): | $\lambda_{max}$: 350 nm |
| | $\epsilon$: 20000 |
| Elemental analysis: | $C_{20}H_{28}O_4$ |

| | C % | H % | O % |
| --- | --- | --- | --- |
| Calculated | 72.26 | 8.49 | 19.25 |
| Found | 72.42 | 8.42 | 19.20 |

EXAMPLE 9

1,4-Bis-[(2',2',4',4'-tetramethyl-5'-oxo-3'-oxa-1'-cyclopentylidene)methyl]benzene

Preparation of a compound of general formula (I') in which $R_1=R_2=R_3=R_4=CH_3, R'_5=R'_7=H$ and $R'_6$ denotes a radical of formula

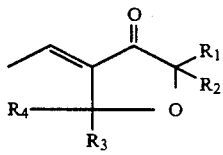

This compound is obtained according to the procedure described in Example I, in which 4-hexyloxybenzaldehyde is replaced by terephthalaldehyde. The product obtained possesses the following characteristics:

| Melting point: | 262° C. |
| --- | --- |
| UV spectrum (chloroform): | $\lambda_{max}$: 330 nm |
| | $\epsilon$: 25000 |
| Elemental analysis: | $C_{24}H_{30}O_4, 0.25\ H_2O$ |

| | C % | H % | O % |
| --- | --- | --- | --- |
| Calculated | 74.51 | 7.89 | 17.59 |
| Found | 74.46 | 7.99 | 17.54 |

EXAMPLE 10

4-[(2',2',4',4'-Tetramethyl-5'-oxo-3'-oxa-1'-cyclopentylidene)methyl]benzoic acid

Preparation of a compound of general formula (I') in which $R_1=R_2=R_3=R_4=CH_3, R'_5=R'_7=H$ and $R'_6=\text{—CO}_2H$ 5 g of the compound obtained in Example 7 are heated for 30 minutes to reflux in 100 cm³ of 50:50 ethanol/water mixture containing 1 g of potassium hydroxide. The reaction mixture is poured into ice-cold water. After acidification by adding 1N hydrochloric acid, filtration of the precipitate, drying and recrystallization in ethyl acetate, the expected product is obtained in the form of pale yellow crystals possessing the following characteristics:

| Melting point | >250° C. |
| --- | --- |
| UV spectrum (dichloromethane): | $\lambda_{max}$: 298 nm |
| | $\epsilon$: 15710 |
| Elemental analysis: | $C_{16}H_{18}O_4$ |

| | C % | H % | O % |
| --- | --- | --- | --- |
| Calculated | 70.06 | 6.61 | 23.33 |
| Found | 69.96 | 6.57 | 23.48 |

APPLICATION EXAMPLES

Example A

| Protective day cream: | |
| --- | --- |
| Compound of Example 1 | 1 g |
| Polyoxyethylated fatty alcohols* | 7 g |
| $C_8$–$C_{12}$ fatty acid triglycerides | 30 g |
| Glycerol monostearate | 2 g |
| Silicone oil | 1.5 g |
| Cetyl alcohol | 1.5 g |
| Preservatives | 0.3 g |
| Fragrance | 0.6 g |
| Demineralized water qs | 100 g |

*Polyoxyethylated fatty alcohols: mixture of cetyl/stearyl alcohol and oxyethylenated cetyl/stearyl alcohol containing 33 moles of ethylene oxide.

For the preparation of this cream, the fats are heated to about 80–85° C; the screening agent of formula (I) is added. Separately, the water is heated to 80–85°C., and the fatty phase is added to the aqueous phase with brisk stirring; the stirring is maintained for 10 to 15 minutes, the mixture is then left to cool with moderate stirring, and fragrance and preservatives are added at about 40° C.

EXAMPLE B

| Protective milk: | |
| --- | --- |
| Compound of Example 4 | 1 g |
| Octyl p-dimethylaminobenzoate | 0.5 g |
| Cetyl/stearyl alcohol | 2 g |
| Cetyl alcohol | 2 g |
| ($C_8$ to $C_{12}$) fatty acid triglycerides | 20 g |
| Lanolin | 4 g |
| Stearic acid | 0.5 g |
| Preservatives | 0.3 g |
| Carbopol 934 (crosslinked polyacrylic acid sold by the company GOODRICH CHEMICAL) | 0.15 g |
| Triethanolamine | 0.2 g |
| Fragrance | 0.4 g |
| Demineralized water qs | 100 g |

The fats are heated to about 80°–85° C; the screening agents are added. Separately, the water is heated to 80°–85 ° C., and the fatty phase is added to the aqueous phase (containing the water-soluble compounds) with brisk stirring; the stirring is continued for 10 to 15 minutes, the mixture is then left to cool with moderate stirring, and fragrance and preservatives are added at about 40° C.

Example C

| Sun cream: | |
| --- | --- |
| Compound of Example 1 | 4 g |
| 4-[(2-Oxo-3-bornylidene)methyl]- | 3.5 g |

-continued

| Sun cream: | |
|---|---|
| phenyltrimethylammonium methylsulphate | |
| Polyoxyethylenated fatty alcohols* | 7 g |
| ($C_8$ to $C_{12}$) fatty acid triglycerides | 30 g |
| Glycerol monostearate | 2 g |
| Silicone oil | 1.5 g |
| Cetyl alcohol | 1.5 g |
| Preservatives, fragrance qs | |
| Demineralized water qs | 100 g |

*Polyoxyethylenated fatty alcohols: mixture of cetyl/stearyl alcohol and oxyethylenated cetyl/stearyl alcohol containing 33 moles of ethylene oxide.

The preparation of this cream is similar to that of Example A, the 4-[(2-oxo-3-bornylidene)methyl]-phenyltrimethylammonium methylammonium methylsulphate being dissolved in the water.

The compound of Example 1 may be replaced by the compound of Example 1 may be replaced by the compound of Example 6.

Example D

| Aqueous-alcoholic sun gel: | |
|---|---|
| Diethanolamine salt of a compound of Example 10 | 1 g |
| Diethanolamine salt of p-methoxycinnamic acid | 2.5 g |
| Carbopol 934 | 0.7 g |
| Triethanolamine | 0.35 g |
| Propylene glycol | 25 g |
| Ethanol, 96° strength | 25 g |
| Preservative | 0.3 g |
| Perfume | 0.4 g |
| Demineralized water qs | 100 g |

The Carbopol is dispersed with brisk stirring in 30 g of water, and the triethanolamine is then added, followed by the solvents and the remainder of the water in which media the screening agents have been dissolved beforehand.

Example E

| Oleo-alcoholic lotion: | |
|---|---|
| Compound of Example 8 | 1.5 g |
| 2-Ethylhexyl p-methoxycinnamate | 2 g |
| Fragrance | 0.5 g |
| Ethanol, 96° strength | 47.5 g |
| ($C_8$ to $C_{12}$) fatty acid triglycerides qs | 100 g |

The mixture of the different constituents is heated to about 40°–45° C. in order to homogenize and obtain a clear lotion. The mixture is allowed to cool and the fragrance is then added.

Example F

| Sun oil: | |
|---|---|
| The following ingredients are mixed, heating, if required, to 40–45° C. in order to homogenize: | |
| Compound of Example 1 | 3 g |
| Octyl p-(dimethylamino)benzoate | 3 g |
| Cocoa butter | 2.5 g |
| Antioxidants | 0.05 g |
| Fragrance | 0.5 g |
| ($C_8$ to $C_{12}$) fatty acid triglycerides qs | 100 g |

The compound of Example 1 may be replaced by 3 g of the compound of Example 4.

Example G

| Sun cream: | |
|---|---|
| The compound of Example 1 | 2.5 g |
| Benzylidenecamphor | 4 g |
| ($C_8$ to $C_{12}$) fatty acid triglycerides | 31 g |
| Glycerol monostearate | 6 g |
| Stearic acid | 6 g |
| Cetyl alcohol | 1.2 g |
| Lanolin | 4 g |
| Preservatives | 0.3 g |
| Propanediol | 2 g |
| Triethanolamine | 0.5 g |
| Fragrance | 0.5 g |
| Demineralized water qs | 100 g |

The emulsion is prepared in the same manner as in Example A.

Example H

| Sun milk: | |
|---|---|
| Compound of Example 1 | 1 g |
| Compound of Example 8 | 3 g |
| Cetyl/stearyl alcohol | 2 g |
| Cetyl alcohol | 2 g |
| ($C_8$ to $C_{12}$) fatty acid triglycerides | 20 g |
| Lanolin | 4 g |
| Stearic acid | 0.5 g |
| Preservatives | 0.3 g |
| Carbopol 934 (crosslinked polyacrylic acid sold by the company GOODRICH CHEMICAL) | 0.15 g |
| Triethanolamine | 0.2 g |
| Fragrance | 0.4 g |
| Demineralized water qs | 100 g |

The emulsion is prepared in the same manner as in Example A.

We claim:

1. A cosmetic sunscreening composition for protecting the skin against ultraviolet radiation of wavelengths between 280 and 380 nm which comprises, in a cosmetically acceptable vehicle, an effective sunscreening concentration of at least one 5-benzylidene-3-oxacyclopentanone derivative having the formula:

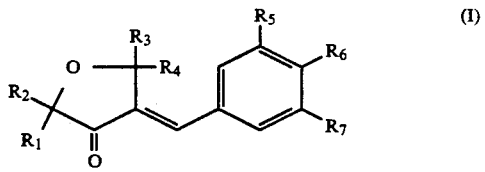

(I)

in which:

$R_1$, $R_2$, $R_3$ and $R_4$, which may be identical or different, denote linear or branched $C_1$–$C_8$ alkyl, aralkyl unsubstituted or substituted with halogen or with $C_1$–$C_4$ alkyl or alkoxy, or aryl unsubstituted or substituted with halogen or $C_1$–$C_4$ alkyl or alkoxy, or alternatively $R_1$ and $R_2$ and/or $R_3$ and $R_4$ form, with the carbon atom to which they are attached, a saturated ring containing 5 or 6 carbon atoms; and $R_5$, $R_6$, and $R_7$, which may be identical or different, denote hydrogen, linear or branched $C_1$–$C_8$ alkyl, linear or branched $C_2$–$C_8$ alkenyloxy, linear or branched $C_2$-$C_{12}$ acyloxy, benzyloxy unsubstituted or substituted with halogen or with $C_1$-$C_4$ alkyl or alkoxy, or —$COOR_{10}$ where $R_{10}$ denotes linear or branched $C_1$-$C_8$ alkyl, hydrogen, alkali metal, or alkaline earth metal, it also being possible for one of the substituents $R_5$, $R_6$, and $R_7$ to denote a radical of formula

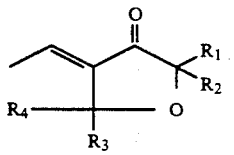

in which $R_1$, $R_2$, $R_3$, and $R_4$ have the meanings stated above, said composition being in a form wherein the cosmetically acceptable vehicle is selected from the group consisting of a lotion, an emulsion, an oil, a gel, a solid stick, and an aerosol.

2. Cosmetic composition according to claim 1 containing 0.25 to 15% by weight of at least one compound of formula (I).

3. cosmetic composition according to claim 1, which comprises at least one compound selected from the group consisting of 5- benzylidene-3-2,2,4,4-thylcyclopentanone, 5-(4'-hexyloxybenzylidene -3-oxa-2,2,4,4tetramethylcyclopentanone, 5-(4'-allyloxybenzylidene)-3-oxa-2,2,4,4-tetramethylcyclopentanone, 5-(4'-octyloxybenzylidene)-3 5-(3', 4', 5'-tribenzyloxybenzylidene)-3-oxa-2,2,4,4tetramethylcyclopentanone, 5-(4'-tert-butoxybenzylidene)3-oxa-2,2,4,4-tetramethylcyclopentanone, 5-(4'-methoxybenzylidene)-3-oxa-2,2,4,4-tetramethylcyclopentanone, 5-(4'-n-butoxy-5'-methoxybenzylidene)-3-oxa-2,2,4,4 -tetramethylcyclopentanone, 1,4 -bis[(2',2',4 ,4'-tetramethyl-5'-oxo-3'-oxa-1,-cyclopentylidene)methyl]benzeneand4-[(2',2',4',4,-tetramethyl-5'-oxo-3'-oxa-1'-cyclopentylidene)methyl]benzoic acid.

4. Cosmetic composition, according to claim 1, which contains, in addition, at least one cosmetic adjuvant selected from the group consisting of thickeners, emollients, humectants, surfactants, preservatives, antifoams, fragrances, oils, waxes, lower monohydric alcohols, polyols, propellants, colourings and 5. Cosmetic composition according to claim 1, in the form of a protective composition for the human epidermis, which contains 0.25 to 3% by weight of at least one compound of formula (I).

6. Cosmetic composition according to claim 1, in the form of an antisun composition, which contains 0.5 to 15% by weight of at least one compound of formula (I).

7. Cosmetic composition according to claim 6, which contains, in addition, other sunscreen agents screening out UV-B or UV-A rays.

* * * * *

UNITED STATES PATENT AND TRADEMARK OFFICE
CERTIFICATE OF CORRECTION

PATENT NO. : 5,217,709
DATED : June 8, 1993
INVENTOR(S) : LAGRANGE ET AL.

It is certified that error appears in the above-indentified patent and that said Letters Patent is hereby corrected as shown below:

IN THE ABSTRACT line 2, "cut" should be --out--.

Column 2, line 59, "1,4-bis[(2',4',4'-tetramethyl-5'-oxo-3,oxa-1'-cyclopentylidene)methyl]benzene", should be -- 1,4-bis[(2',2',4',4'-tetramethyl-5'-oxo-3'-oxa-1'-, cyclopentylidene)methyl]benzene --.

Column 3, line 43, "$C_2C_{12}$" should be -- $C_2-C_{12}$ --.

Column 3, line 62, "(I,)" should be -- (I') --.

Column 6, line 54, "...2,2,4,4-tetramethv-" should be -- ...2,2,4,4-tetramethy- --.

Column 7, line 26, "prosesses" should be --possesses --.

Column 7, line 64, "$R_1=R_2=R_3=R_4=CH_3,=CH_3,R'_5=R'_7=H$" should be --$R_1=R_2=R_3=R_4=CH_3, R'_5=R'_7=H$ --.

Column 8, line 12, between the tables, insert the following:

UNITED STATES PATENT AND TRADEMARK OFFICE
CERTIFICATE OF CORRECTION

PATENT NO. : 5,217,709
DATED : June 8, 1993
INVENTOR(S) : Lagrange et al.

It is certified that error appears in the above-identified patent and that said Letters Patent is hereby corrected as shown below:

-- EXAMPLE 5

5-(3',4',5'-Tribenzyloxybenzylidene)-3-oxa-2,2,4,4 - tetramethylcyclopentanone

Preparation of a compound of general formula (I') in which $R_1=R_2=R_3=R_4=CH_3$ and $R'_5=R'_6=R'_7=O-CH_2-C_6H_5$ This compound is obtained according to the procedure described in Example 1, in which 4-hexyloxybenzaldehyde is replaced by 3,4,5-tribenzyloxybenzaldehyde. The product obtained possesses the following characteristics: --

Column 11, line 16, delete the second occurrence of "methylammonium".

Column 11, lines 19-20, delete "1 may be replaced by the compound of Example"

Column 12, last line, after "$C_2-C_8$", insert --alkenyl, linear or branched $C_1-C_{12}$ alkoxy, linear or branched $C_2-C_{12}$--.

Signed and Sealed this

Eighth Day of February, 1994

Attest:

BRUCE LEHMAN

Attesting Officer    Commissioner of Patents and Trademarks